United States Patent [19]
McCormick

[11] Patent Number: 5,846,945
[45] Date of Patent: *Dec. 8, 1998

[54] CYTOPATHIC VIRUSES FOR THERAPY AND PROPHYLAXIS OF NEOPLASIA

[75] Inventor: Francis McCormick, Richmond, Calif.

[73] Assignee: ONYX Pharmaceuticals, Inc., Richmond, Calif.

[ * ] Notice: The term of this patent shall not extend beyond the expiration date of Pat. No. 5,677,178.

[21] Appl. No.: 485,037

[22] Filed: Jun. 7, 1995

Related U.S. Application Data

[63] Continuation of Ser. No. 198,184, Feb. 16, 1994, abandoned, which is a continuation-in-part of Ser. No. 17,525, Feb. 16, 1993, abandoned.

[51] Int. Cl.$^6$ .............................. C12N 5/10; C12N 7/01; C07H 21/04; A61K 31/70
[52] U.S. Cl. ................ 514/44; 435/235.1; 435/370.1; 435/325; 435/375; 536/23.1; 536/24.1
[58] Field of Search ........................ 514/44; 435/320.1, 435/325, 235.1, 375; 536/23.1, 24.1

[56] References Cited

FOREIGN PATENT DOCUMENTS

| 2051289 | 9/1991 | Canada . |
| WO 93/19191 | 9/1993 | WIPO . |
| WO 96/00007 | 1/1996 | WIPO . |

OTHER PUBLICATIONS

Orkin "Report & Recommendation of the Panel to Assess the NIH Investment in Research on Gene Therapy", 1995.
Shepherd et al., J. of Virology, 67(5):2944–2949 (1993).
Chang et al., British J. Cancer, 68(4):653–661 (1993).
Subramanian et al., Cell Growth & Differentiation, 6:131–137 (1995).
Barker et al, Virology, 156:107–121 (1989).
Barbeau et al., Oncogene, 9(2):359–373 (1994).
Phelps et al., J. of Virology, 66(4):2418–2427 (1992).
Brokaw et al., Virology, 205:603–607 (1994).
Shingu et al., J. Gen Virol., 72:2031–2034 (1991).
Martuza et al., Science, 252:854–856 (1991).
Horwitz, "Adenoviral Diseases" in Virology, Fields et al, eds., Raven Press (New York), 477–495 (1985).
Whyte et al., Cell, 56:67–75 (1989).
Cote et al, Cancer Research, 51:5410–5436 (1991).
Maxwell et al, Cancer Research, 46:4660–4664 (1986).
Brody et al, Am. Rev. Respir. Dis., 145:425A (1992).
Graham et al, Methods in Molecular Biology, 7:109–128 (1991).
Smith et al., Studies on the Use of Viruses in the Treatment of Carcinoma of the Cervix, *Cancer*, vol. 9, pp. 1211–1218 (1956).
Newman et al., Virus Treatment in Advanced Cancer, *Cancer*, vol. 7, pp. 106–118, (1954).
Alice E. Moore, Effects of Viruses on Tumors, *Ann Rev Microbiol*, vol. 8, pp. 393–410 (1954).

(List continued on next page.)

*Primary Examiner*—Nancy Degen
*Attorney, Agent, or Firm*—Gregory J. Giotta, Ph.D.

[57] ABSTRACT

Methods and compositions for treating neoplastic conditions by viral-based therapy are provided. Mutant virus lacking viral proteins which bind and/or inactivate p53 or RB are administered to a patient having a neoplasm which comprises cells lacking p53 and/or RB function. The mutant virus is able to substantially produce a replication phenotype in neoplastic cells but is substantially unable to produce a replication phenotype in non-replicating, non-neoplastic cells having essentially normal p53 and/or RB function. The preferential generation of replication phenotype in neoplastic cells results in a preferential killing of the neoplastic cells, either directly or by expression of a cytotoxic gene in cells expressing a viral replication phenotype.

5 Claims, 9 Drawing Sheets

OTHER PUBLICATIONS

F.L. Graham, Transformation by and Oncogenicity of Human Adenoviruses, The Adenoviruses, Chapter 9, pp. 339–383 (1984).

Bjorn et al., Selective Elimination of Breast Cancer Cells from Human Bone Marrow Using an Antibody–Pseudomonas, Cancer Research, vol. 50, pp. 5992–5996, (1990).

Crook et al., Degradation of p53 Can Be Targeted by HPV E6 Sequences Distinct from Those Required for p53 Binding and Trans–activation. Cell, vol. 67, pp. 547–556 (1991).

Mietz et al., The Transcriptional transactivation function of wild–type p53 is inhibited by SV40 large T–antigen and by HPV–16 E6 oncoprotein. EMBO, vol. 11, pp. 5013–5020 (1992).

CYTOPATHIC VIRUSES FOR THERAPY AND PROPHYLAXIS OF NEOPLASIA

This application is a continuation of U.S. Ser. No. 08/198,184, filed Feb. 16, 1994, now abandoned, which is a continuation-in-part of U.S. Ser. No. 08/017,525, filed Feb. 16, 1993, now abandoned.

TECHNICAL FIELD

The invention provides compositions of recombinant cytopathic viruses which are capable of replication and/or expression of late region genes in neoplastic mammalian cells but are essentially non-replicable in non-neoplastic cells, methods for constructing and propagating such recombinant viruses, methods for treating neoplastic disease with such recombinant viruses, and therapeutic compositions comprising such recombinant viruses.

BACKGROUND

The proliferation of normal cells is thought to be regulated by growth-promoting proto-oncogenes counterbalanced by growth-constraining tumor-suppressor genes. Mutations that potentiate the activities of proto-oncogenes create the oncogenes that force the growth of neoplastic cells. Conversely, genetic lesions that inactivate tumor suppressor genes, generally through mutation(s) that lead to a cell being homozygous for the inactivated tumor suppressor allele, can liberate the cell from the normal replicative constraints imposed by these genes. Usually, an inactivated tumor suppressor gene (e.g., p53, RB, DCC, NF-1) in combination with the formation of an activated oncogene (i.e., a proto-oncogene containing an activating structural or regulatory mutation) can yield a neoplastic cell capable of essentially unconstrained growth (i.e., a transformed cell).

Oncogenic transformation of cells leads to a number of changes in cellular metabolism, physiology, and morphology. One characteristic alteration of oncogenically transformed cells is a loss of responsiveness to constraints on cell proliferation and differentiation normally imposed by the appropriate expression of cell- growth regulatory genes.

While different types of genetic alterations may all lead to altered expression or function of cell-growth regulatory genes and to abnormal growth, it is generally believed that more than one event is required to lead to neoplastic transformation of a normal cell to a malignant one (Land et al. (1983) *Nature* 304: 596; Weinberg R A (1989) *Cancer Res.* 49: 3713). The precise molecular pathways and secondary changes leading to malignant transformation for most cell types are not clear. A number of cases have been reported in which altered expression or activity of some proteins with putative cell-cycle control functions and/or implicated in the formation of functional transcriptional complexes, such as p53 and RB, can lead to loss of proliferation control in cells (Ullrich et al. (1992) *J. Biol. Chem.* 267: 15259; Hollstein et al. (1991) *Science* 253: 49; Sager R (1992) *Curr. Opin. Cell. Biol.* 4: 155; Levine et al. (1991) *Nature* 351: 453).

Some oncogenes have been found to possess characteristic activating mutations in a significant fraction of certain cancers. For example, particular mutations in the $ras^H$ and $ras^K$ coding regions (e.g., codon 12, codon 61; Parada et al. (1984) *Nature* 312: 649) and the APC gene (Powell et al. (1992) *Nature* 359: 235) are associated with oncogenic transformation of cultured cells and are present in a striking percentage of specific human cancers (e.g., colon adenocarcinoma, bladder carcinoma, lung carcinoma and adenocarcinoma, hepatocarcinoma). These findings have led to the development of diagnostic and therapeutic reagents (e.g., polynucleotide probes and antibodies) that specifically recognize the activated form(s) of such oncogenes (U.S. Pat. No. 4,798,787 and U.S. Pat. No. 4,762,706).

The excessive or inappropriate expression of other oncogenes, such as myc, erbB-2, and pim-1, appears to be able to potentiate oncogenic transformation without necessarily requiring the presence of activating mutation(s) in the coding region. Overexpression of erbB-2 is frequently found in adenocarcinoma of the breast, stomach, and ovary, and erbB-2 levels in these cell types might serve as a diagnostic marker for neoplasia and/or may correlate with a specific tumor phenotype (e.g., resistance to specific drugs, growth rate, differentiation state).

Transgenic animals harboring various oncogenes (U.S. Pat. No. 4,736,866 and U.S. Pat. No. 5,087,571) or functionally disrupted tumor suppressor genes (Donehower et al. (1992) *Nature* 356: 215) have been described for use in carcinogen screening assays, among other potential uses.

Despite this progress in developing a more defined model of the molecular mechanisms underlying the transformed phenotype and neoplasia, few significant therapeutic methods applicable to treating cancer beyond conventional chemotherapy have resulted. Many conventional chemotherapeutic agents have a low therapeutic index, with therapeutic dosage levels being at or near dosage levels which produce toxicity. Toxic side effects of most conventional chemotherapeutic agents are unpleasant and lead to life-threatening bone marrow suppression, among other side effects.

Recent approaches for performing gene therapy to correct or supplement defective alleles which cause congenital diseases, such as cystic fibrosis, have been attempted with reports of limited initial success. Some gene therapy approaches involve transducing a polynucleotide sequence capable of expressing a functional copy of a defective allele into a cell in vivo using replication-deficient recombinant adenovirus (Rosenfeld et al. (1992) *Cell* 68: 143). Some of these gene therapy methods are efficient at transducing polynucleotides into isolated cells explanted from a patient, but have not been shown to be highly efficient in vivo. Therapeutic approaches to cancer which rely on transfection of explanted tumor cells with polynucleotides encoding tumor necrosis factor (TNF) and interleukin-2 (IL-2) have been described (Pardoll D (1992) *Curr. Opin. Oncol.* 4: 1124).

Although it might someday prove possible for gene therapy methods to be adapted to correct defective alleles of oncogenes or tumor suppressor genes in transformed cells in vivo, present gene therapy methods have not been reported to be able to efficiently transduce and correctly target (e.g., by homologous recombination) a sufficient percentage of neoplastic cells for practical gene therapy of neoplasia in situ. The nature of cancer biology mandates that a substantial fraction of the neoplastic cells, preferably all of the clonal progeny of the transformed cell, are ablated for an effective therapeutic effect. Moreover, present methods for gene therapy are very expensive, requiring ex vivo culturing of explanted cells prior to reintroduction into a patient. Widespread application of such methods, even if they were effective, would be prohibitively expensive.

Thus there exists a need in the art for methods and compositions for diagnosis and therapy of neoplastic diseases, especially for methods which selectively ablate neoplastic cells without the undesirable killing of non-neoplastic cells that is typical of conventional antineoplastic chemotherapy. The present invention fulfills these and other needs.

The references discussed herein are provided solely for their disclosure prior to the filing date of the present application. Nothing herein is to be construed as an admission that the inventors are not entitled to antedate such disclosure by virtue of prior invention.

SUMMARY OF THE INVENTION

The present invention provides several novel methods and compositions for ablating neoplastic cells by infecting the neoplastic cells with a recombinant adenovirus which is substantially replication deficient in non-neoplastic cells and which exhibits at least a partial replication phenotype in neoplastic cells. The difference in replication phenotype of the adenovirus constructs of the invention in neoplastic and non-neoplastic cells provides a biological basis for viral-based therapy of cancer. Expression of adenoviral cytopathic effects, and optionally expression of a negative-selectable drug-gene (e.g., HSV tk), are correlated with the adenoviral replication phenotype characteristic of neoplastic cells infected with the recombinant adenovirus constructs of the invention, thus discriminating between neoplastic and non-neoplastic cells and providing selective cytotoxicity of neoplastic cells. Although the methods are described in detail specifically for adenoviral constructs, the methods are believed to be applicable to essentially any virus type wherein efficient replication requires binding and/or sequestration and/or inactivation of a host cell protein that is present in non-neoplastic cells but is substantially absent or nonfunctional in neoplastic cells (e.g., p53, RB).

In order for adenovirus to replicate efficiently in cells, the adenoviral E1b gene product, p55, forms a complex with the host cell p53 protein, thereby sequestering and/or inactivating p53 and producing a cell that is deficient in p53 function. Such a cell made deficient in p53 function can support replication of the adenovirus. In this way, wild-type adenovirus is able to replicate in cells containing p53, as the adenovirus p55 proteins inactivates and/or sequesters the host cell p53 protein. In one embodiment of the invention, a recombinant adenovirus comprising an E1b locus encoding a mutant p55 protein that is substantially incapable of forming a functional complex with p53 protein in infected cells is administered to an individual or cell population comprising a neoplastic cell capable of being infected by the recombinant adenovirus. The substantial incapacity of the recombinant adenovirus to effectively sequester p53 protein in infected non-neoplastic cells results in the introduced recombinant adenoviral polynucleotide(s) failing to express a replication phenotype in non-neoplastic cells. By contrast, neoplastic cells which lack a functional p53 protein support expression of a replication phenotype by the introduced recombinant adenovirus which leads to ablation of the neoplastic cell by an adenoviral cytopathic effect and/or expression of a negative selection gene linked to the replication phenotype. In preferred variations of these embodiments, the recombinant adenovirus comprises an E1b locus encoding a mutant p55 which is substantially incapable of binding p53 and may optionally also lack a functional p19 protein (i.e., incapable of inhibiting expression of adenoviral early region genes in the presence of E1a polypeptides). Recombinant adenoviruses of the invention may further comprise a mutant p19 gene which produces enhanced cytopathic effects; such a mutant known in the art is the p19 cyt mutant gene. However, it may be preferable to retain functional p19 in some mutants to maintain the integrity of viral DNA during the infection.

In an alternative embodiment of the invention, a recombinant adenovirus comprising an E1a locus encoding an E1a protein (e.g., p289R or p243R) that is substantially incapable of forming a complex with RB protein in infected cells is administered to an individual or cell population comprising a neoplastic cell capable of being infected by the recombinant adenovirus. The substantial incapacity of the recombinant adenovirus to effectively sequester RB protein in infected non-neoplastic cells results in the introduced recombinant adenoviral polynucleotide(s) failing to express a replication phenotype in non-neoplastic cells. By contrast, neoplastic cells which lack a functional RB protein support expression of a replication phenotype by the introduced recombinant adenovirus which leads to ablation of the neoplastic cell by an adenoviral cytopathic effect and/or expression of a negative selection gene linked to the replication phenotype. In preferred variations of these embodiments, the recombinant adenovirus comprises an E1a locus encoding a mutant E1a protein (e.g., p289R) that lacks a CR1 and/or CR2 domain capable of binding RB (and/or the 300 kD polypeptide and/or the 107 kD polypeptide) but comprises a functional CR3 domain capable of transactivation of adenoviral early genes. Additional variations of these embodiments include those where the recombinant adenovirus comprises a nonfunctional E1a locus which is substantially incapable of expressing a protein that binds to and inactivates RB and may optionally also comprise a functional p19 protein (i.e., capable of stimulating expression of adenoviral early region genes in the absence of E1a function). Recombinant adenoviruses of the invention may further comprise a mutant p19 gene which produces enhanced cytopathic effects; such a mutant known in the art is the p19 cyt mutant gene.

The invention provides novel recombinant adenovirus constructs which are replication defective in non-neoplastic cells but capable of expressing a replication phenotype in neoplastic cells lacking functional p53 and/or RB. The novel recombinant adenovirus constructs comprise a mutation, such as a deletion or point mutation, in the E1a and/or E1b gene regions, especially in the sequences encoding the E1b p55 protein and the CR1 and CR2 domains of the E1a p289R or p243R proteins. In some embodiments, a negative selectable gene, such as an HSV tk gene, is operably linked to an early region (e.g., E2, E1a, E1b) enhancer/promoter, a late region gene enhancer/promoter (e.g., major late promoter), or an early or late region promoter with a CMV enhancer, in a recombinant adenovirus construct also comprising an E1a or E1b mutation, so that the negative selectable gene is preferentially transcribed in infected cells which express a replication phenotype (i.e., neoplastic cells) and provides negative selection of such cells by administration of an effective dosage of a negative selection agent (e.g., gancyclovir, FIAU). A negative selectable gene may be inserted in place of an E1a and/or E1b structural sequence to concomitantly form an E1a$^{(-)}$ replication deficient mutant, E1b$^{(-)}$ replication deficient mutant, or E1a/E1b double mutant, respectively.

Antineoplastic compositions comprising such recombinant adenovirus in a pharmaceutically acceptable form for delivery to a neoplastic cell population in vivo are also provided.

The invention also provides recombinant papovaviruses, such as human papillomavirus (HPV), polyomaviruses (e.g., BK, JC) and SV40, which lack functional proteins for binding and/or inactivating p53 and/or RB. Human papillomavirus mutants lacking expression of functional E6 protein will substantially lack the capacity to effectively degrade p53 and thus will be capable of manifesting a replication phenotype in p53$^{(-)}$ cells but not in cells containing a sufficient level of functional p53. Human papillomavirus mutants lacking expression of functional E7 protein will substantially lack the capacity to effectively bind RB and thus will be capable of manifesting a replication phenotype in RB$^{(-)}$ cells but not in cells containing a sufficient level of functional RB. Human papillomavirus mutants lacking expression of both functional E6 protein and functional E7 protein will substantially lack the capacity to effectively bind RB and p53 thus will be capable of manifesting a replication phenotype in p53$^{(-)}$ RB$^{(-)}$ cells but not in cells containing a sufficient level of functional RB and/or p53.

The invention also provides novel methods for treating a neoplastic disease comprising the steps of administering to a patient a recombinant virus capable of preferentially expressing a replication phenotype and/or expressing a cytopathic effect in a neoplastic cell population as compared to expression in a non-neoplastic cell population.

BRIEF DESCRIPTION OF THE DRAWING

FIG. 2(a–i) shows infection of normal and neoplastically transformed human cell lines with wild-type adenovirus and recombination-deficient recombinant adenovirus mutants. Each cell line indicated was mock-infected, FIG. 2(a); or infected at an MOI of 1.0 with wild-type adenovirus 2, FIG. 2(b–c); mutant derivative dl 1010, FIG. 2(d–e); mutant derivative dl 1520, FIG. 2(f–g); or mutant derivative dl 434, FIG. 2(h–i). FIG. 2(b), 4 days; FIG. 2(c), 7 days; FIG. 2(d), 8 days; FIG. 2(e), 12 days; FIG. 2(f), 14 days; FIG. 2(g), 20 days; FIG. 2(h), 6 days; FIG. 2(i), 14 days. On various days post-infection (noted supra), the cells were washed with PBS to remove dead cells and the remaining cells were stained with crystal violet. Each cell line mock infected with PBS alone was included as a control for viability.

FIG. 3(a–c) shows infection of the normal human lung diploid fibroblast cell line IMR90 (ATCC CCL 186) with wildtype and mutant adenoviruses. IMR90 cells were infected with the indicated virus at MOIs corresponding to 0.1, 1.0, 10, and 100. At the indicated days post-infection, cells were washed with PBS and stained with crystal violet. One well in each 6-well dish was seeded with 293 cells to serve as a positive control for virus infection.

DEFINITIONS

Figure 1:
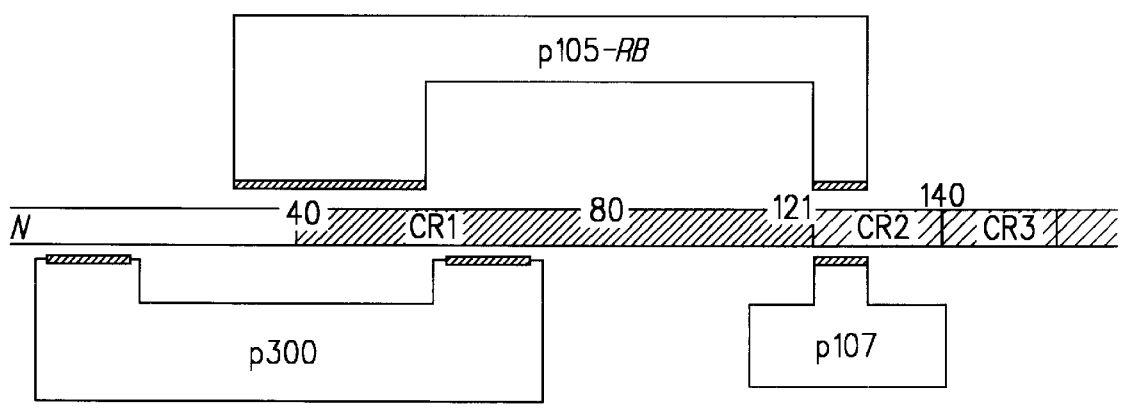
FIG. 1 shows a schematic representation of the domain structure and protein-protein interactions of an adenovirus E1a-289R polypeptide.
Figure 2A:
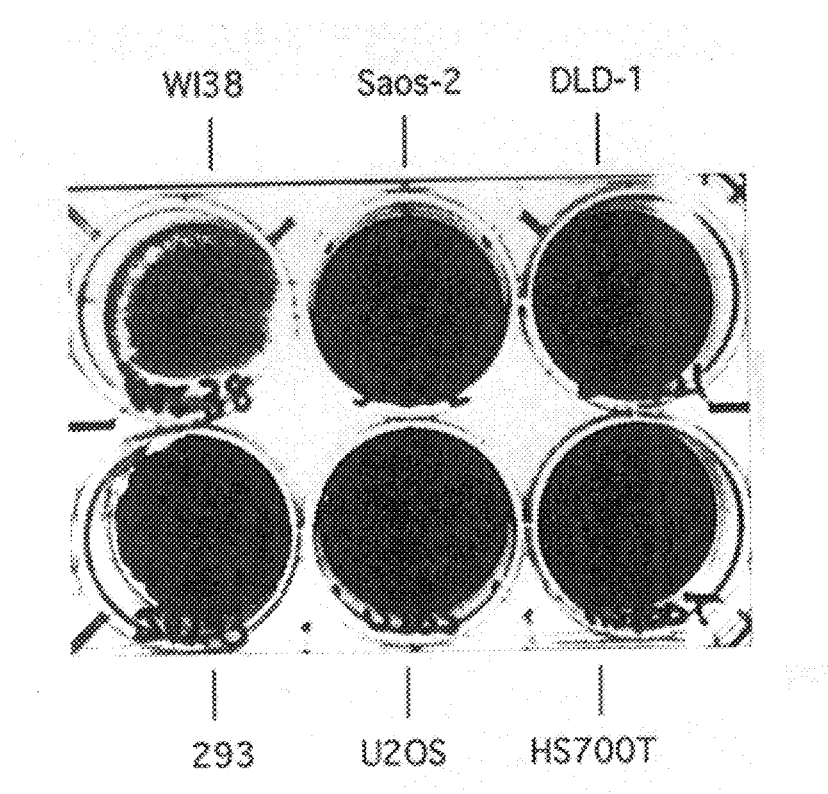
FIG. 2(a) shows results 9 days after the mock infection. The remaining panels show results from the following post-infection periods.
Figure 2B:
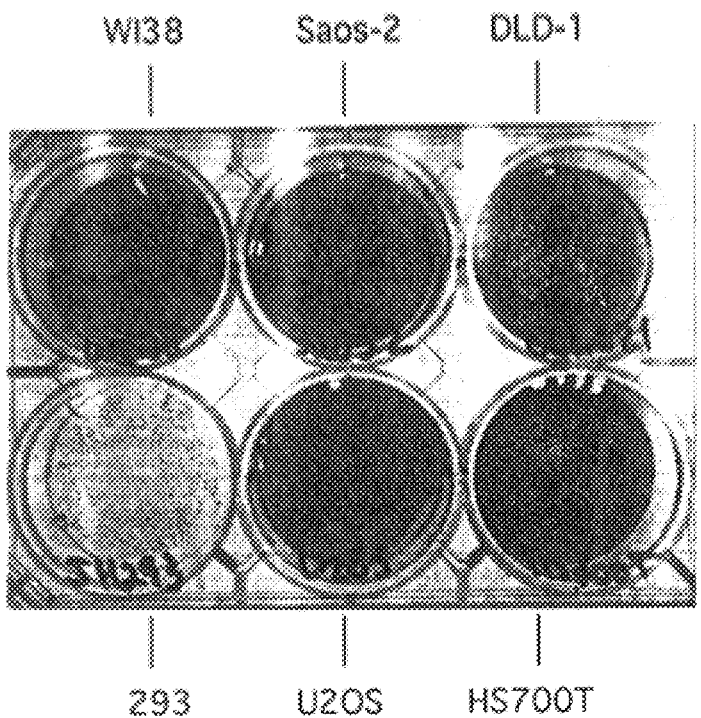
Figure 2C:
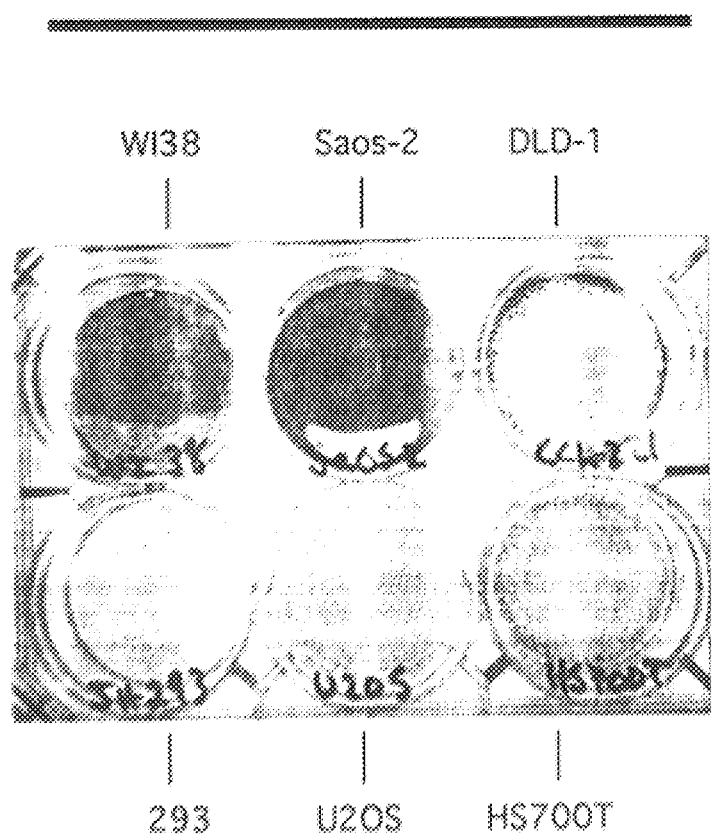
Figure 2D:
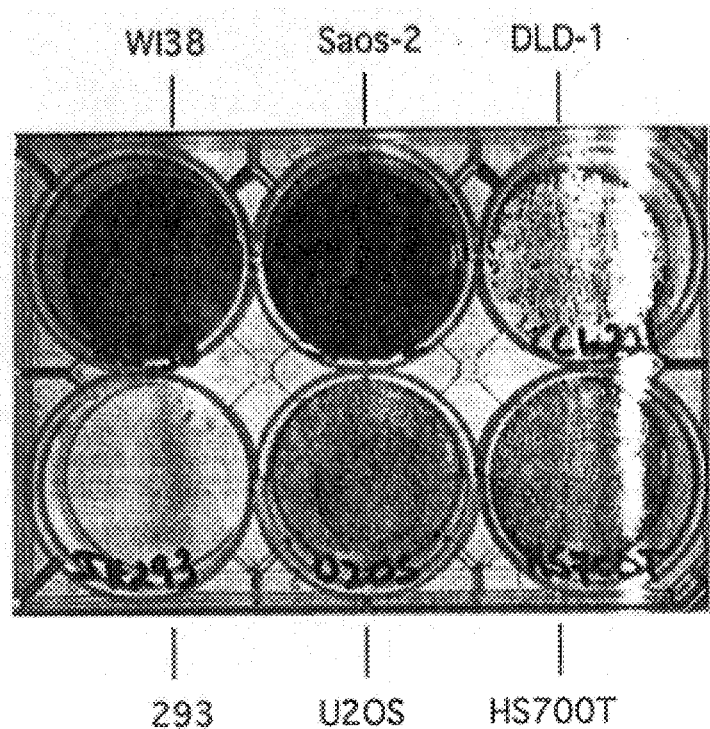
Figure 2E:
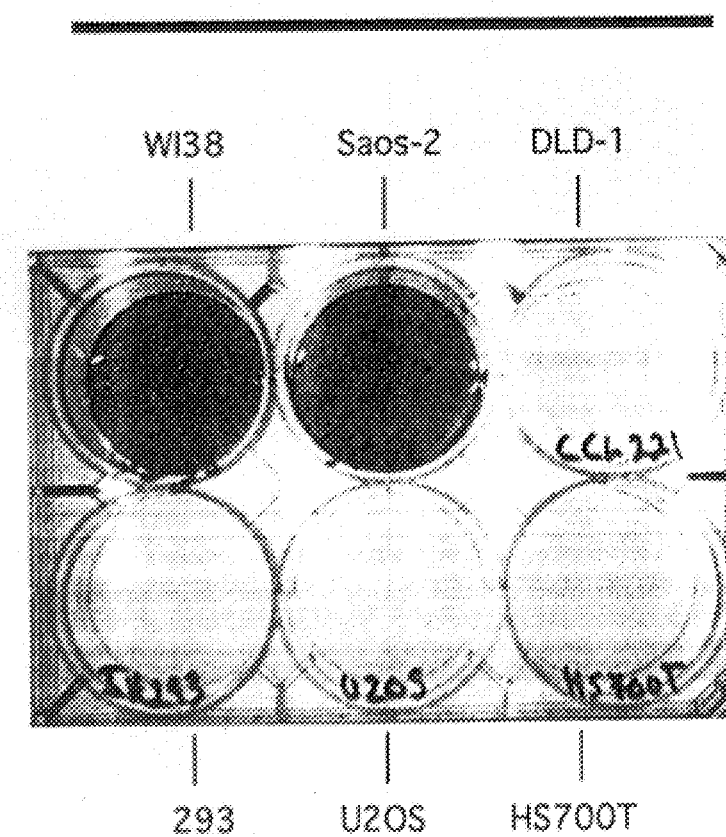
Figure 2F:
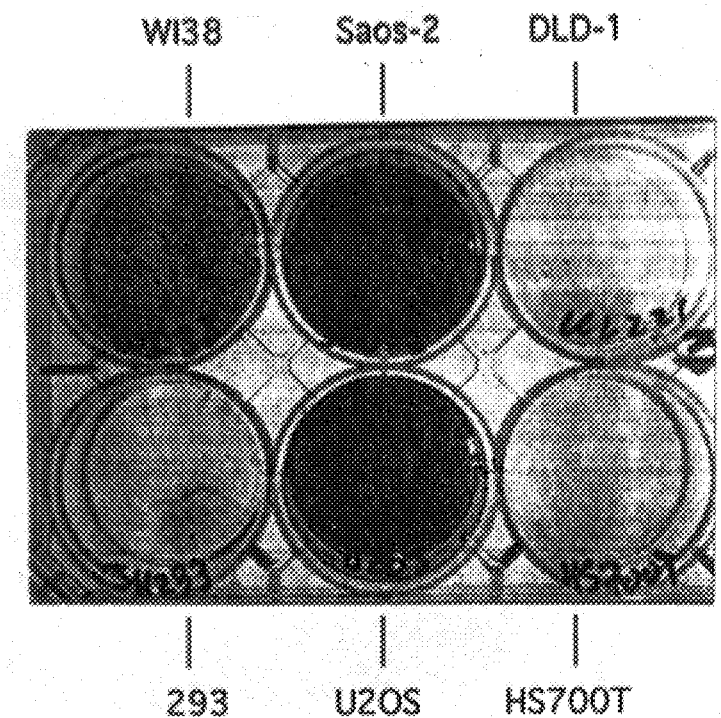
Figure 2G:
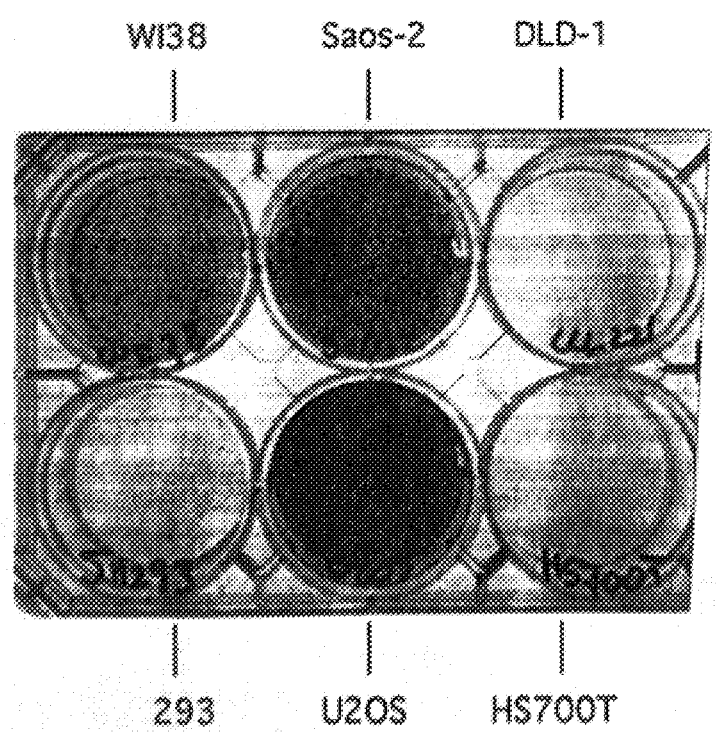
Figure 2H:
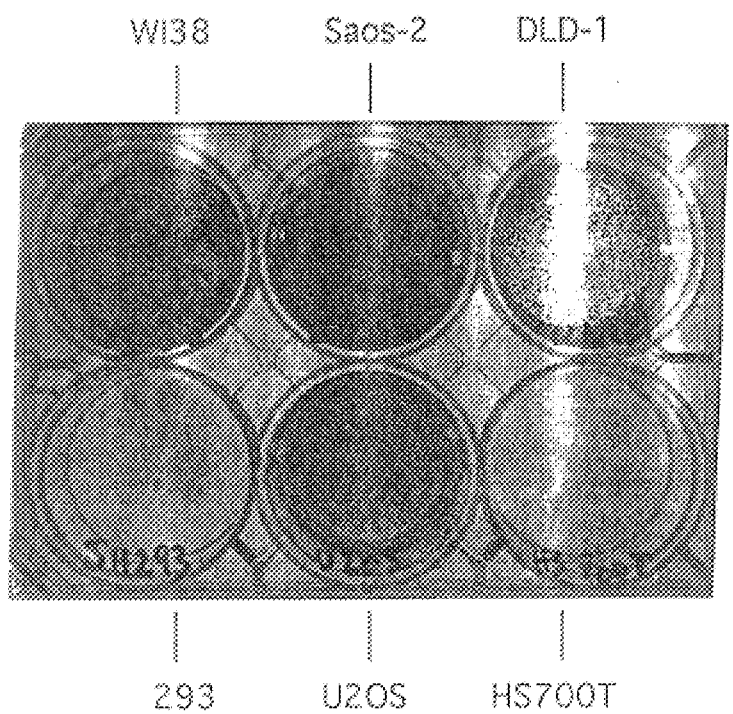
Figure 2I:
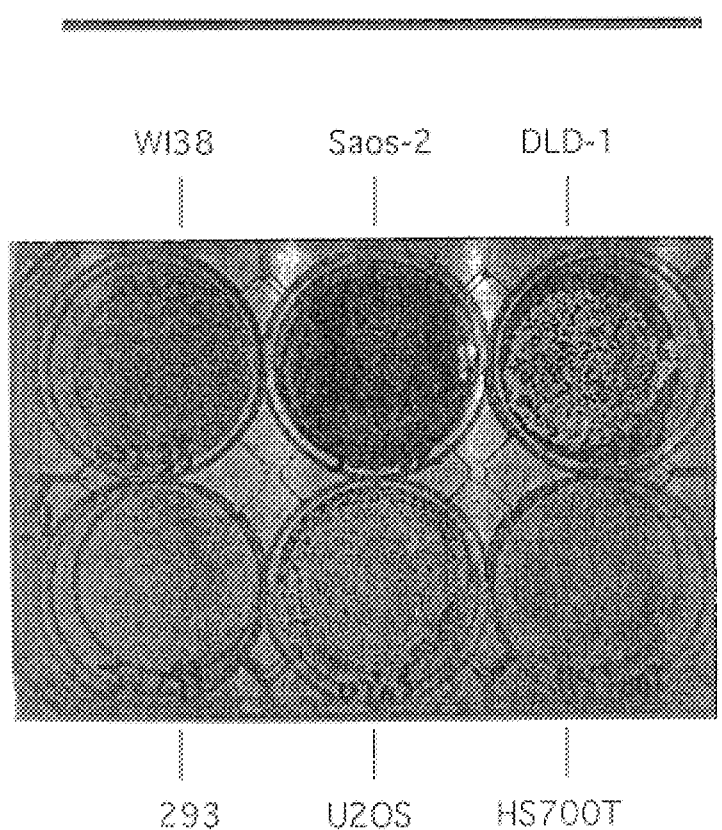

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. As used herein, the term "recombinant" indicates that a polynucleotide construct (e.g., and adenovirus genome) has been generated, in part, by intentional modification by man.

As used herein, the term "replication deficient virus" refers to a virus that preferentially inhibits cell proliferation or induces apoptosis in a predetermined cell population (e.g., cells substantially lacking p53 and/or RB function) which supports expression of a virus replication phenotype, and which is substantially unable to inhibit cell proliferation, induce apoptosis, or express a replication phenotype in cells comprising normal p53 and RB function levels characteristic of non-replicating, non-transformed cells. Typically, a replication deficient virus exhibits a substantial decrease in plaquing efficiency on cells comprising normal RB and/or p53 function.

As used herein, the term "p53 function" refers to the property of having an essentially normal level of a polypeptide encoded by the p53 gene (i.e., relative to non-neoplastic cells of the same histological type), wherein the p53 polypeptide is capable of binding an E1b p55 protein of wild-type adenovirus 2 or 5. For example, p53 function may be lost by production of an inactive (i.e., mutant) form of p53 or by a substantial decrease or total loss of expression of p53 polypeptide(s). Also, p53 function may be substantially absent in neoplastic cells which comprise p53 alleles encoding wild-type p53 protein; for example, a genetic alteration outside of the p53 locus, such as a mutation that results in aberrant subcellular processing or localization of p53 (e.g., a mutation resulting in localization of p53 predominantly in the cytoplasm rather than the nucleus) can result in a loss of p53 function.

As used herein, the term "RB function" refers to the property of having an essentially normal level of a polypeptide encoded by the RB gene (i.e., relative to nonneoplastic cells of the same histological type), wherein the RB polypeptide is capable of binding an E1a protein of wildtype adenovirus 2 or 5. For example, RB function may be lost by production of an inactive (i.e., mutant) form of RB or by a substantial decrease or total loss of expression of RB polypeptide(s). Also, RB function may be substantially absent in neoplastic cells that comprise RB alleles encoding a wildtype RB protein; for example, a genetic alteration outside of the RB locus, such as a mutation that results in aberrant subcellular processing or localization of RB, may result in a loss of RB function.

As used herein, the term "replication phenotype" refers to one or more of the following phenotypic characteristics of cells infected with a virus such as a replication deficient adenovirus: (1) substantial expression of late gene products, such as capsid proteins (e.g., adenoviral penton base polypeptide) or RNA transcripts initiated from viral late gene promoter(s), (2) replication of viral genomes or formation of replicative intermediates, (3) assembly of viral capsids or packaged virion particles, (4) appearance of cytopathic effect (CPE) in the infected cell, (5) completion of a viral lytic cycle, and (6) other phenotypic alterations which are typically contingent upon abrogation of p53 or RB function in non-neoplastic cells infected with a wild-type replication competent DNA virus encoding functional oncoprotein(s). A replication phenotype comprises at least one of the listed phenotypic characteristics, preferably more than one of the phenotypic characteristics.

The term "antineoplastic replication deficient virus" is used herein to refer to a recombinant virus which has the functional property of inhibiting development or progression of a neoplasm in a human, by preferential cell killing of infected neoplastic cells relative to infected non-replicating, non-neoplastic cells of the same histological cell type.

As used herein, "neoplastic cells" and "neoplasia" refer to cells which exhibit relatively autonomous growth, so that they exhibit an aberrant growth phenotype characterized by a significant loss of control of cell proliferation. Neoplastic cells comprise cells which may be actively replicating or in a temporary non-replicative resting state ($G_1$ or $G_0$); similarly, neoplastic cells may comprise cells which have a well-differentiated phenotype, a poorly-differentiated phenotype, or a mixture of both type of cells. Thus, not all neoplastic cells are necessarily replicating cells at a given timepoint. The set defined as neoplastic cells consists of cells in benign neoplasms and cells in malignant (or frank) neoplasms. Frankly neoplastic cells are frequently referred to as cancer, typically termed carcinoma if originating from cells of endodermal or ectodermal histological origin, or sarcoma if originating from cell types derived from mesoderm.

As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame. However, since enhancers generally function when separated from the promoter by several kilobases and intronic sequences may be of variable lengths, some polynucleotide elements may be operably linked but not contiguous.

As used herein, "physiological conditions" refers to an aqueous environment having an ionic strength, pH, and temperature substantially similar to conditions in an intact mammalian cell or in a tissue space or organ of a living mammal. Typically, physiological conditions comprise an aqueous solution having about 150 mM NaCl (or optionally KCl), pH 6.5–8.1, and a temperature of approximately 20°–45° C. Generally, physiological conditions are suitable binding conditions for intermolecular association of biological macromolecules. For example, physiological conditions of 150 mM NaCl, pH 7.4, at 37° C. are generally suitable.

DETAILED DESCRIPTION

Generally, the nomenclature used hereafter and the laboratory procedures in cell culture, molecular genetics, and molecular virology described below are those well known and commonly employed in the art. Standard techniques are used for recombinant nucleic acid methods, polynucleotide synthesis, polypeptide synthesis, generation and propagation of virus stocks (including cell lines capable of transcomplementation of replication deficient virus stocks), cell culture, and the like. Generally enzymatic reactions and purification steps are performed according to the manufacturer's specifications. The techniques and procedures are generally performed according to conventional methods in the art and various general references (see, generally, Sambrook et al. Molecular Cloning: A Laboratory Manual, 2d ed. (1989) Cold Spring Harbor Laboratory Press, Cold Spring Harbor, N.Y.; *Virology*, Second edition, eds. Fields BN and Knipe DM, (1990) Raven Press, New York, N.Y., incorporated herein by reference) which are provided throughout this document. The procedures therein are believed to be well known in the art and are provided for the convenience of the reader. All the information contained therein is incorporated herein by reference.

Neoplasia is a pathological condition which is characterized, in part, by the generation of neoplastic cells having variant genotypes and phenotypes. Some tumors may comprise a population of cells lacking RB function but having p53 function; such cells are designated $RB^{(-)}$. Some tumor cells may lack p53 function but have RB function; such cells are designated $p53^{(-)}$. Some tumors may comprise cells lacking both p53 and RB and are designated $p53^{(-)} RB^{(-)}$. The cell line SAOS2 (infra, see Experimental Example) is an example of a neoplastic cell type which is $p53^{(-)} RB^{(-)}$. Also, there may be neoplastic cells which comprise essentially normal levels of p53 and RB; such cells having both normal p53 and normal RB may lack other oncoproteins (e.g., tumor suppressor gene products other than p53 or RB) which can provide the basis for antineoplastic viral constructs which can preferentially manifest a replication phenotype in such neoplastic cells.

A basis of the present invention is that several DNA viruses which infect mammalian cells (e.g., adenoviruses; papovaviruses such as BK and JC, SV40, and papillomaviruses such as HPV, and the like) encode viral proteins which are essential for efficient progression through the viral replication cycle; some of these viral proteins sequester cellular proteins, such as those involved in cell-cycle control and/or formation of transcription complexes, as a necessary condition for efficient viral replication. In the absence of the viral proteins which bind, sequester, or degrade such cellular proteins as p53 and RB, viral replication is substantially inhibited. Normal (i.e., non-neoplastic) cells which are infected with a mutant virus lacking the ability to sequester or degrade p53 and/or RB are generally unable to support replication of the mutant virus, hence such mutant viruses are considered to be replication deficient (or replication defective). However, since the sequestration or degradation of p53 or RB is not necessary for viral replication in cells which lack functional p53 or RB (such cells are designated $p53^{(-)}$ and $RB^{(-)}$ respectively) it is possible that replication deficient mutant viruses which are defective for p53 and/or RB sequestration or degradation may express a replication phenotype in such $p53^{(-)}$ or $RB^{(-)}$ cells to a greater extent than in cells having essentially normal p53 and/or RB function. Neoplastic cells frequently lack p53 function (a $p53^{(-)}$ cell), RB function (a $RB^{(-)}$ cell), or both functions (a $p53^{(-)} RB^{(-)}$ cell). Hence, some replication deficient viral mutants may preferentially exhibit a replication phenotype in neoplastic cells.

Viral mutants lacking the capacity to express a functional RB inactivating protein (e.g., adenovirus E1a, HPV E7 protein) will manifest a replication phenotype in $RB^{(-)}$ cells and $RB^{(-)} p53^{(-)}$ cells. Viral mutants lacking the capacity to express a functional p53 inactivating protein (e.g., adenovirus E1b p55, HPV E6 protein) will manifest a replication phenotype in $p53^{(-)}$ cells and $RB^{(-)} p53^{(-)}$ cells. Viral mutants lacking the capacity to express both a functional p53 inactivating protein (e.g., adenovirus E1b p55, HPV E6 protein) and a functional RB inactivating protein (e.g., adenovirus E1a, HPV E7 protein) will manifest a replication phenotype in $RB^{(-)} p53^{(-)}$ cells. Cytotoxicity linked to the expression of a replicative phenotype can therefore be used as a basis for preferentially killing neoplastic cells having a $RB^{(-)}$, $p53^{(-)}$, or $RB^{(-)} p53^{(-)}$ phenotype. Although some replicating non-neoplastic cells may transiently exhibit a $RB^{(-)}$ phenotype, $p53^{(-)}$ phenotype, or $RB^{(-)} p53^{(-)}$ phenotype during progression through the cell cycle, the viral mutants of the invention may be used for preferential, albeit not necessarily completely selective, killing of neoplastic cells, thus constituting a useful antineoplastic therapy modality to be used alone or in combination with other modalities of treatment. Deletions (or other inactivating mutations) in the 37 amino-terminal residues of the HPV E7 polypeptide are preferred HPV mutants for application to RB$^{(-)}$ cells, since these residues are important for RB binding.

Although the methods and compositions presented below are described specifically for methods relating to replication deficient adenoviral constructs, it is believed that the invention can be practiced with other DNA viruses encoding oncoproteins which sequester or enhance the degradation of p53 protein or RB protein, for example replication deficient papillomavirus species (e.g., mutants of HPV types 16, 18, 33) that contain mutations in the E6 and/or E7 genes which substantially abrogate p53 and/or RB function, respectively. In addition to members of the family Adenoviridae (specifically the genus Mastadenovirus), it is believed that members of the family Papovaviridae, especially papillomavirus and polyomavirus, which encode viral proteins that sequester and/or inactivate p53 or RB are suitable for use in the methods of the invention.

For a general description of adenovirus and papovavirus biology, *Virology,* Second edition, eds. Fields B N and Knipe D M, Vol.2, pp. 1651–1740, Raven Press, New York, N.Y., incorporated herein by reference, may be referred to for guidance. The following specific descriptions refer to, but are not limited to, adenovirus serotype 5 and adenovirus serotype 2. Although it is believed that other adenoviral serotypes may be used, adenovirus type 5 provides a common reference point for the nucleotide numbering convention of viral polynucleotides and amino acid numbering of viral-encoded polypeptides of the E1a viral gene region, and other viral genes. Adenovirus type 2 provides a convenient reference for the numbering convention of the E1b viral gene region, and other viral gene regions. It is believed that those of skill in the art will readily identify the corresponding positions in other adenoviral serotypes. References to human papillomavirus generally refer to a type associated with neoplasia (e.g., types 16, 18, or 33), although non-oncogenic types may also be used.

E1a Mutants

The loss of retinoblastoma tumor suppressor gene (RB) gene function has been associated with the etiology of various types of tumors. The product of this tumor suppressor gene, a 105 kilodalton polypeptide called pRB or p105, is a cell-cycle regulatory protein. The pRB polypeptide inhibits cell proliferation by arresting cells at the $G_1$ phase of the cell cycle. The pRB protein is also a major target of several DNA virus oncoproteins, including adenovirus E1a, SV40 large T Ag, and papillomavirus E7. These viral proteins bind and inactivate pRB, and the function of inactivating pRB is important in facilitating viral replication. The pRB protein interacts with the E2F transcription factor, which is involved in the expression of the adenovirus E2 gene and several cellular genes, and inhibits the activity of this transcription factor (Bagchi et al. (1991) *Cell* 65: 1063; Bandara et al. (1991) *Nature* 351: 494; Chellappan et al. (1992) *Proc. Natl. Acad. Sci. (U.S.A.)* 89: 4549, incorporated herein by reference). The viral oncoproteins, such as adenovirus E1a, disrupt the pRB/E2F complex resulting in activation of E2F. However, cells lacking sufficient functional pRB to complex the E2F will not require the presence of a functional oncoprotein, such as E1a, to possess transcriptionally active E2F. Therefore, it is believed that replication deficient adenovirus species which lack the capacity to complex RB but substantially retain other essential replicative functions will exhibit a replication phenotype in cells which are deficient in RB function (e.g., cells which are homozygous or heterozygous for substantially deleted RB alleles, cells which comprise RB alleles encoding mutant RB proteins which are essentially nonfunctional, cells which comprise mutations that result in a lack of function of an RB protein) but will not substantially exhibit a replicative phenotype in non-replicating, non-neoplastic cells. Such replication deficient adeniovirus species are referred to herein for convenience as E1a-RB$^{(-)}$ replication deficient adenoviruses.

A cell population (such as a mixed cell culture or a human cancer patient) which comprises a subpopulation of neoplastic cells lacking RB function and a subpopulation of non-neoplastic cells which express essentially normal RB function can be contacted under infective conditions (i.e., conditions suitable for adenoviral infection of the cell population, typically physiological conditions) with a composition comprising an infectious dosage of a E1a-RB$^{(-)}$ replication deficient adenovirus. Such contacting results in infection of the cell population with the E1a-RB$^{(-)}$ replication deficient adenovirus. The infection produces preferential expression of a replication phenotype in a significant fraction of the cells comprising the subpopulation of neoplastic cells lacking RB function but does not produce a substantial expression of a replicative phenotype in the subpopulation of non-neoplastic cells having essentially normal RB function. The expression of a replication phenotype in an infected RB$^{(-)}$ cell results in the death of the cell, such as by cytopathic effect (CPE), cell lysis, apoptosis, and the like, resulting in a selective ablation of neoplastic RB$^{(-)}$ cells from the cell population.

Typically, E1a-RB$^{(-)}$ replication deficient adenovirus constructs suitable for selective killing of RB$^{(-)}$ neoplastic cells comprise mutations (e.g., deletions, substitutions, frameshifts) which inactivate the ability of an E1a polypeptide to bind RB protein effectively. Such inactivating mutations typically occur in the E1a CR1 domain (amino acids 30–85 in Ad5: nucleotide positions 697–790) and/or the CR2 domain (amino acids 120–139 in Ad5; nucleotide positions 920–967), which are involved in binding the p105 RB protein and the p107 protein. Preferably, the CR3 domain (spanning amino acids 150–186) remains and is expressed as a truncated p289R polypeptide and is functional in transactivation of adenoviral early genes. FIG. 1 portrays schematically the domain structure of the E1a-289R polypeptide.

Suitable E1a-RB$^{(-)}$ replication deficient adenovirus constructs for use in the methods and compositions of the invention include, but are not limited to the following examples: (1) adenovirus serotype 5 NT dl 1010, which encodes an E1a protein lacking the CR1 and CR2 domains (deletion of amino acids 2 to 150; nucleotides 560–1009) necessary for efficient RB binding, but substantially retaining the CR3 domain (Whyte et al. (1989) *Cell* 56: 67, incorporated herein by reference), and (2) adenovirus serotype 5 dl 312, which comprises a deleted viral genome lacking the region spanning nucleotides 448–1349 which encodes the entire E1a region in wild-type adenovirus (Jones N and Shenk T (1979) *Proc. Natl. Acad. Sci. (U.S.A.)* 76: 3665, incorporated herein by reference). Ad5 NT dl 1010 is a preferred E1a-RB$^{(-)}$ replication deficient adenovirus and is available from Dr. E. Harlow, Massachusetts General Hospital, Boston, Mass.).

It may be preferable to incorporate additional mutations into such adenovirus constructs to inhibit formation of infectious virions in neoplastic cells which otherwise would support replication of the E1a-RB$^{(-)}$ mutants. Such additional inactivating mutations would be preferred in therapeutic modalities wherein complete viral replication forming infectious virions capable of spreading to and infecting adjacent cells is undesirable. These fully inactivated mutants are referred to as nonreplicable E1a-RB$^{(-)}$ mutants. Such nonreplicable mutants comprise mutations which prevent formation of infectious virions even in p53$^{(-)}$ RB$^{(-)}$ cells; such mutations typically are structural mutations in an essential virion protein or protease.

However, in many modalities it is desirable for the mutant virus to be replicable and to form infectious virions containing the mutant viral genome which may spread and infect other cells, thus amplifying the antineoplastic action of an initial dosage of mutant virus.

Additional E1a$^{(-)}$ mutants lacking the capacity to bind RB can be generated by those of skill in the art by generating mutations in the E1a gene region encoding E1a polypeptides, typically in the CR1 and/or CR2 domains, expressing the mutant E1a polypeptide, contacting the mutant E1a polypeptides with p105 or a binding fragment of RB under aqueous binding conditions, and identifying mutant E1a polypeptides which do not specifically bind RB as being candidate E1a$^{(-)}$ mutants suitable for use in the invention. Alternative assays include contacting the mutant E1a polypeptides with the 300 kD protein and/or p107 protein or binding fragment thereof under aqueous binding conditions, and identifying mutant E1a polypeptides which do not specifically bind the 300 kD and/or p107 polypeptides as being candidate E1a$^{(-)}$ mutants suitable for use in the invention. Alternative binding assays include determining the inability of E1a$^{(-)}$ mutant protein (or absence of E1a protein) to form complexes with the transcription factor E2F and/or to lack the ability to dissociate the RB protein from RB:E2F complexes under physiological conditions (Chellappan et al. (1991) op.cit., incorporated herein by reference).

Alternative functional assays for determining mutants lacking E1a function, such as loss of transctivation by E1a of transcription of various reporter polypeptides linked to a E1a-dependent transcriptional regulatory sequence, and the like, will be used.

E1b Mutants

A function of the cellular phosphoprotein p53 is to inhibit the progression of mammalian cells through the cell cycle. Wild-type adenovirus E1b p55 protein binds to p53 in infected cells that have p53 and produce a substantial inactivation of p53 function, likely by sequestering p53 in an inactive form. Functional E1b p55 protein is essential for efficient adenoviral replication in cells containing functional p53. Hence, adenovirus variants which substantially lack the ability to bind p53 are replication deficient in non-replicating, non-neoplastic cells having normal levels of functional p53.

Human tumor cells frequently are homozygous or heterozygous for mutated (e.g., substitution, deletion, frameshift mutants) p53 alleles, and lack p53 function necessary for normal control of the cell cycle (Hollstein et al. (1991) *Science* 253: 49; Levine et al. (1991) op.cit., incorporated herein by reference). Thus, many neoplastic cells are p53$^{(-)}$, either because they lack sufficient levels of p53 protein and/or because they express mutant forms of p53 which are incapable of substantial p53 function, and which may substantially diminish p53 function even when wild-type p53 may be present (e.g., by inhibiting formation of functional multimers). Some neoplastic cells may comprise alleles encoding essentially wild-type p53 proteins, but may comprise a second site mutation that substantially abrogates p53 function, such as a mutation that results in p53 protein being localized in the cytoplasm rather than in the nucleus; such second site mutants also substantially lack p53 function.

It is believed that replication deficient adenovirus species which lack the capacity to complex p53 but substantially retain other essential viral replicative functions will exhibit a replication phenotype in cells which are deficient in p53 function (e.g., cells which are homozygous for substantially deleted p53 alleles, cells which comprise mutant p53 proteins which are essentially nonfunctional) but will not substantially exhibit a replicative phenotype in non-replicating, non-neoplastic cells. Such replication deficient adenovirus species are referred to herein for convenience as E1b-p53$^{(-)}$ replication deficient adenoviruses.

A cell population (such as a mixed cell culture or a human cancer patient) which comprises a subpopulation of neoplastic cells lacking p53 function and a subpopulation of non-neoplastic cells which express essentially normal p53 function can be contacted under infective conditions (i.e., conditions suitable for adenoviral infection of the cell population, typically physiological conditions) with a composition comprising an infectious dosage of a E1b-p53$^{(-)}$ replication deficient adenovirus. Such contacting results in infection of the cell population with the E1b-p53$^{(-)}$ replication deficient adenovirus. The infection produces preferential expression of a replication phenotype in a significant fraction of the cells comprising the subpopulation of neoplastic cells lacking p53 function but does not produce a substantial expression of a replicative phenotype in the subpopulation of non-neoplastic cells having essentially normal p53 function. The expression of a replication phenotype in an infected p53$^{(-)}$ cell results in the death of the cell, such as by cytopathic effect (CPE), cell lysis, apoptosis, and the like, resulting in a selective ablation of neoplastic p53$^{(-)}$ cells from the cell population.

Typically, E1b-p53$^{(-)}$ replication deficient adenovirus constructs suitable for selective killing of p53$^{(-)}$ neoplastic cells comprise mutations (e.g., deletions, substitutions, frameshifts) which inactivate the ability of the E1b p55 polypeptide to bind p53 protein effectively. Such inactivating mutations typically occur in the regions of p55 which bind p53. Optionally, the mutant E1b region may encode and express a functional p19 protein encoded by the E1b region remains and that is functional in transactivation of adenoviral early genes in the absence of E1a polypeptides.

Suitable E1b-p53$^{(-)}$ replication deficient adenovirus constructs for use in the methods and compositions of the invention include, but are not limited to the following examples: (1) adenovirus type 2 dl 1520, which contains a C to T mutation at nucleotide position 2022 that generates a stop codon 3 amino acids downstream of the AUG codon used for initiation of translation of the p55 protein and a deletion between nucleotides 2496 and 3323 replaced with a small linker insertion that generates a second stop codon at nucleotide 3336; the expression of the p19 protein is essentially unaffected (Barker and Berk (1987) *Virology* 156: 107, incorporated herein by reference, and (2) a composite adenovirus construct comprising adenovirus type 2 dl 1520 comprising at least the position 2022 mutation and/or the 2496–3323 deletion mutation, or a substantial portion thereof, and an additional mutation in p19 to yield a p19 cyt mutant; the composite virus construct lacks p55 and comprises the enhanced cytopathic effect of the p19 cyt mutation. Ad2 dl 1520 are available from Dr. A. Berk, University of California at Los Angeles, Los Angeles, Calif., and are described in the literature, including Barker and Berk (1987) *Virology* 156: 107, incorporated herein by reference.

It may be preferable to incorporate additional mutations into such adenovirus constructs to inhibit formation of infectious virions in neoplastic cells which otherwise would support replication of the E1b-p53$^{(-)}$ mutants. Such additional inactivating mutations would be preferred in therapeutic modalities wherein complete viral replication forming infectious virions capable of spreading to and infecting adjacent cells is undesirable. These fully inactivated mutants are referred to as nonreplicable E1b-p53$^{(-)}$ mutants. Such nonreplicable mutants comprise mutations which prevent formation of infectious virions even in p53$^{(-)}$ RB$^{(-)}$ cells; such mutations typically are structural mutations in an essential virion protein or protease.

However, in many modalities it is desirable for the mutant virus to be replicable and to form infectious virions containing the mutant viral genome which may spread and infect other cells, thus amplifying the antineoplastic action of an initial dosage of mutant virus.

Additional E1b$^{(-)}$ mutants lacking the capacity to bind p53 can be generated by those of skill in the art by generating mutations in the E1b gene region encoding the p55 polypeptide, expressing mutant p55 polypeptides, contacting the mutant p55 polypeptides with p53 or a binding fragment of p53 under aqueous binding conditions, and identifying mutant E1b polypeptides which do not specifically bind p53 as being candidate E1b$^{(-)}$ mutants suitable for use in the invention.

More typically, a functional assay will be used to identify candidate E1b$^{(-)}$ mutants. For example, the Friend assay for determination of p53 function will be performed essentially as described in Frebourg et al. (1992) *Cancer Res.* 52: 6977, incorporated herein by reference. E1b mutants which lack the capacity to inactivate p53 will be identified as candidate E1b$^{(-)}$ replication deficient mutants.

E1a/E1b Double Mutants

Some human tumor cells lack both p53 function and RB function, either by mutational inactivation or deletion of one or both protein species. Such cells are termed p53$^{(-)}$ RB$^{(-)}$ cells.

It is believed that replication deficient adenovirus species which lack the capacity to bind p53 and which also lack the capacity to bind RB, but which substantially retain other essential viral replicative functions will preferentially exhibit a replication phenotype in p53$^{(-)}$ RB$^{(-)}$ cells. Such replication deficient adenovirus species are referred to herein for convenience as E1a-RB$^{(-)}$/E1b-p53$^{(-)}$ replication deficient adenoviruses, or simply E1a/E1b double mutants. Such E1a/E1b double mutants can be constructed by those of skill in the art by combining at least one E1a-RB$^{(-)}$ mutation in the E1a region and at least one E1b-p53$^{(-)}$ mutation in E1b region encoding p55 to form a E1a/E1b double mutant adenovirus. Such a replication deficient double mutant adenovirus will exhibit a replication phenotype in cells which are deficient in both p53 and RB functions but will not substantially exhibit a replicative phenotype in non-replicating, non-transformed cells or in cells which are deficient in either p53 or RB function but not both functions. For example, the Ad5 dl 434 mutant (Grodzicker et al. (1980) *Cell* 21: 454, incorporated herein by reference) comprises a deletion of the E1a locus and a partial deletion of the E1b locus, and substantially lacks the capacity to encode functional E1a and E1b p55 proteins.

A cell population (such as a mixed cell culture or a human cancer patient) which comprises a subpopulation of neoplastic cells lacking p53 and RB functions and a subpopulation of non-neoplastic cells which express essentially normal p53 function and/or RB function can be contacted under infective conditions (i.e., conditions suitable for adenoviral infection of the cell population, typically physiological conditions) with a composition comprising an infectious dosage of a replication deficient E1a/E1b double mutant adenovirus. Such contacting results in infection of the cell population with the E1a/E1b double mutant replication deficient adenovirus. The infection produces preferential expression of a replication phenotype in a significant fraction of the cells comprising the subpopulation of neoplastic cells lacking both p53 function and RB function but does not produce a substantial expression of a replicative phenotype in the subpopulation of non-neoplastic cells having essentially normal p53 function and/or RB function. The expression of a replication phenotype in an infected p53$^{(-)}$ RB$^{(-)}$ cell results in the death of the cell, such as by cytopathic effect (CPE), cell lysis, and the like, resulting in a selective ablation of neoplastic p53$^{(-)}$ RB$^{(-)}$ cells from the cell population.

It may be preferable to incorporate additional mutations into such adenovirus constructs to inhibit formation of infectious virions in neoplastic cells which otherwise would support replication of an E1a/E1b double mutant. Such additional inactivating mutations would be preferred in therapeutic modalities wherein complete viral replication forming infectious virions capable of spreading to and infecting adjacent cells is undesirable. These fully inactivated mutants are referred to as nonreplicable E1a/ E1b double mutants. Such nonreplicable mutants comprise mutations which prevent formation of infectious virions even in p53()RB$^{(-)}$ cells; such mutations typically are structural mutations in an essential virion protein or protease.

However, in many modalities it is desirable for the mutant virus to be replicable and to form infectious virions containing the mutant viral genome which may spread and infect other cells, thus amplifying the antineoplastic action of an initial dosage of mutant virus.

Negative Selection Viral Constructs

Although expression of an adenoviral replication phenotype in an infected cell correlates with viral-induced cytotoxicity, generally by cell lysis, cytopathic effect (CPE), apoptosis, or other mechanisms of cell death, it may often be preferable to augment the cytotoxicity of a recombinant adenovirus that is to be used for antineoplastic therapy. Such augmentation may take the form of including a negative selection gene in the recombinant adenovirus, typically operably linked to an adenoviral promoter which exhibits positive transcriptional modulation in cells expressing a replication phenotype. For example, a HSV tk gene cassette may be operably linked immediately downstream of an E3 promoter of a replication deficient adenovirus, such as Ad5 NT dl 1110. Frequently, it is desirable to delete a nonessential portion (i.e., for viral replication and packaging) of the adenoviral genome to accommodate the negative selection cassette; thus a substantial portion of the E3 gene region may be deleted and replaced with a negative selection cassette such as an HSV tk gene operably linked to an E2 promoter (and enhancer) or other suitable promoter/enhancer. Alternatively, a negative selection gene may be operably linked to an adenovirus late region promoter to afford efficient expression of the negative selection gene product in cells expressing a replication phenotype characterized by transcription from late gene promoters.

For embodiments where viral replication forming infectious virions in vivo is undesirable, adenovirus replication deficient constructs which are nonreplicable are used. Such nonreplicable mutants comprise an E1a$^{(-)}$ and/or E1b$^{(-)}$ mutation and comprise all genetic functions necessary for generating a replication phenotype in a suitable neoplastic cell (e.g., a p53$^{(-)}$ cell, a RB$^{(-)}$ cell, or a p53$^{(-)}$RB$^{(-)}$ cell) but have deleted at least one essential gene function necessary for formation of infectious virions, such as structural coat proteins, proteases, and the like. Alternatively, an elicited immune response evoked by the virus may neutralize infectious virions and moderate spread of the viral infection. Nonreplicable mutants lacking a complementable trans-acting function in addition to an E1a and/or E1b mutation may be propagated in conjunction with a complementary helper virus or a helper cell line capable of providing the deleted trans-acting function(s). For example, the 293 cell line (ATCC # CRL 1573; Graham et al. (1977) *J. Gen. Virol.* 36: 59, incorporated herein by reference) which provides E1a and E1b functions in trans may be modified to provide additional functions in trans, such as a virion coat protein or the like, to permit propagation of the "nonreplicable" mutants for developing virus stocks.

Expression of the HSV tk gene in a cell is not directly toxic to the cell, unless the cell is exposed to a negative selection agent such as gancyclovir or FIAU. Infected cells expressing a replication phenotype wherein a negative selection gene is substantially expressed may produce essentially no additional cytotoxicity until the negative selection agent (e.g., gancyclovir) is administered in an effective selective dosage, at which time the infected cells expressing the tk gene will be selectively ablated; thus negative selection can be used for enhanced cytopathic killing and/or to damp out further viral replication by killing cells exhibiting a replicative phenotype. Further, by adjusting the dosages and/or administration schedule of the negative selection agent, it is possible to produce only a partial ablation of the infected cell population expressing the negative selection gene. Generally, the dosage of gancyclovir is calibrated by generating a standard dose-response curve and determining the dosage level at which a desired level of ablation of infected neoplastic cells is observed. Information regarding administration of gancyclovir (GANC) to animals is available in various sources in the art, including human prescribing directions from package inserts. When used in cell culture, a selective concentration of gancyclovir is typically in the range of 0.05 $\mu$M to 50 $\mu$M, typically about 1 $\mu$M, with about 0.2 $\mu$M used for in vitro applications and about 1–5 $\mu$M administered for in vivo applications (typically administered over about 24 hours by continuous infusion from an osmotic pump loaded with 125 mg/ml of gancyclovir in aqueous solution). A dosage schedule for in vivo administration may comprise gancyclovir at a dosage of 5 mg/kg bodyweight B.I.D., given intravenously for seven days.

Negative selection genes may be incorporated into E1a-RB$^{(-)}$ replication deficient adenovirus constructs, E1ba-p53$^{(-)}$ replication deficient adenoviral constructs, E1a/E1b double mutant replication deficient viral constructs, or the like. A preferred embodiment is an HSV tk gene cassette (Zjilstra et al. (1989) *Nature* 342:435; Mansour et al. (1988) Nature 336: 348; Johnson et al. (1989) *Science* 245: 1234; Adair et al. (1989) *Proc. Natl. Acad. Sci (U.S.A.)* 86: 4574; Capecchi, M. (1989) *Science* 244:1288, incorporated herein by reference) operably linked to the E2 promoter of Ad5 NT dl1110 or an alternative promoter and/or enhancer (e.g., major late promoter, E1a promoter/enhancer, E1b promoter/enhancer), with a polydenylation site to form a tk expression cassette. The tk expression cassette (or other negative selection expression cassette) is inserted into the adenoviral genome, for example, as a replacement for a substantial deletion of the E3 gene. Other negative selection genes and replication deficient adenovirus constructs will be apparent to those of skill in the art. It is believed that a negative selection gene operably linked to the E2 promoter is an especially preferred embodiment for incorporation into E1a$^{(-)}$ replication-deficient adenovirus mutants, as the E2 promoter contains multiple E2F sites, whereas RB$^{(-)}$ and p53$^{(-)}$RB$^{(-)}$ lack RB function and presumably will exhibit more efficient transcription from the E2 promoter.

Diagnostic and In Vitro Uses

The replication deficient adenoviruses of the invention may be used to detect the presence of cells lacking p53 and/or RB function. For example, a cell sample comprising a subpopulation of neoplastic cells lacking p53 and/or RB can be infected with a suitable replication deficient adenovirus species. After a suitable incubation period, the cells in the cell sample that express a replication phenotype (e.g., loss of ability to exclude Trypan blue, virion formation, $^3$H-thymidine incorporation into viral DNA) can be quantified to provide a measure of the number or proportion of replicative and/or neoplastic cells in the cell sample. Such methods may be used to diagnose neoplasms and/or evaluate tumor cell load following chemotherapy in a patient on the basis of an explanted cell sample (e.g., a lymphocyte sample from a patient undergoing chemotherapy for a lymphocytic leukemia).

Alternative diagnostic uses and variations are apparent; for example, a reporter gene (e.g., luciferase, $\beta$-galactosidase) may be substituted for a negative selection gene in a replication deficient adenovirus; transformed cells may be scored (such as in a cellular sample or transformation assay) by the expression of the reporter gene, which is correlated with expression of a replication phenotype indicating a lack of p53 and/or RB in a cell.

Therapeutic Methods

Therapy of neoplastic disease may be afforded by administering to a patient a composition comprising replication defective adenoviruses of the invention, including: E1a-RB$^{(-)}$ replication deficient adenoviruses, E1b-p53$^{(-)}$ replication deficient adenoviruses, E1a/E1b double mutants, and replication deficient adenoviruses further comprising a negative selection gene.

Various human neoplasms comprising cells that lack p53 and/or RB functions may be treated with the replication deficient adenoviral constructs. For example but not limitation, a human patient or nonhuman mammal having a bronchogenic carcinoma, nasopharyngeal carcinoma, laryngeal carcinoma, small cell and non-small cell lung carcinoma, lung adenocarcinoma, hepatocarcinoma, pancreatic carcinoma, bladder carcinoma, colon carcinoma, breast carcinoma, cervical carcinoma, ovarian carcinoma, or lymphocytic leukemias may be treated by administering an effective antineoplastic dosage of an appropriate replication deficient adenovirus. Suspensions of infectious adenovirus particles may be applied to neoplastic tissue by various routes, including intravenous, intraperitoneal, intramuscular, subdermal, and topical. A adenovirus suspension containing about $10^3$ to $10^{12}$ or more virion particles per ml may be inhaled as a mist (e.g., for pulmonary delivery to treat bronchogenic carcinoma, small-cell lung carcinoma, non-small cell lung carcinoma, lung adenocarcinoma, or laryngeal cancer) or swabbed directly on a tumor site for treating a tumor (e.g., bronchogenic carcinoma, nasopharyngeal carcinoma, laryngeal carcinoma, cervical carcinoma) or may be administered by infusion (e.g., into the peritoneal cavity for treating ovarian cancer, into the portal vein for treating hepatocarcinoma or liver metastases from other non-hepatic primary tumors) or other suitable route, including direct injection into a tumor mass (e.g., a breast tumor), enema (e.g., colon cancer), or catheter (e.g., bladder cancer).

Candidate antineoplastic adenovirus mutants may be further evaluated by their capacity to reduce tumorigenesis or neoplastic cell burden in nu/nu mice harboring a transplant of neoplastic cells lacking p53 and/or RB function, as compared to untreated mice harboring an equivalent transplant of the neoplastic cells.

Antineoplastic replication deficient adenovirus mutants may be formulated for therapeutic and diagnostic administration to a patient having a neoplastic disease. For therapeutic or prophylactic uses, a sterile composition containing a pharmacologically effective dosage of one or more species of antineoplastic replication deficient adenovirus mutant is administered to a human patient or veterinary nonhuman patient for treatment of a neoplastic condition. Generally, the composition will comprise about $10^3$ to $10^{15}$ or more adenovirus particles in an aqueous suspension. A pharmaceutically acceptable carrier or excipient is often employed in such sterile compositions. A variety of aqueous solutions can be used, e.g., water, buffered water, 0.4% saline, 0.3% glycine and the like. These solutions are sterile and generally free of particulate matter other than the desired adenoviral virions. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. Excipients which enhance infection of cells by adenovirus may be included.

Replication deficient viruses may be delivered to neoplastic cells by liposome or immunoliposome delivery; such delivery may be selectively targeted to neoplastic cells on the basis of a cell surface property present on the neoplastic cell population (e.g., the presence of a cell surface protein which binds an immunoglobulin in an immunoliposome). Typically, an aqueous suspension containing the virions are encapsulated in liposomes or immunoliposomes. For example, a suspension of replication deficient adenovirus virions can be encapsulated in micelles to form immunoliposomes by conventional methods (U.S. Pat. No. 5,043,164, U.S. Pat. No. 4,957,735, U.S. Pat. No. 4,925,661; Connor and Huang (1985) *J. Cell Biol.* 101: 582; Lasic D D (1992) *Nature* 355: 279; *Novel Drug Delivery* (eds. Prescott L F and Nimmo W S: Wiley, N.Y., 1989); Reddy et al. (1992) *J. Immunol.* 148: 1585; incorporated herein by reference). Immunoliposomes comprising an antibody that binds specifically to a cancer cell antigen (e.g., CALLA, CEA) present on the cancer cells of the individual may be used to target virions to those cells.

The compositions containing the present antineoplastic replication deficient adenoviruses or cocktails thereof can be administered for prophylactic and/or therapeutic treatments of neoplastic disease. In therapeutic application, compositions are administered to a patient already affected by the particular neoplastic disease, in an amount sufficient to cure or at least partially arrest the condition and its complications. An amount adequate to accomplish this is defined as a "therapeutically effective dose" or "efficacious dose." Amounts effective for this use will depend upon the severity of the condition, the general state of the patient, and the route of administration.

In prophylactic applications, compositions containing the antineoplastic replication deficient adenoviruses or cocktails thereof are administered to a patient not presently in a neoplastic disease state to enhance the patient's resistance to recurrence of a neoplasm or to prolong remission time. Such an amount is defined to be a "prophylactically effective dose." In this use, the precise amounts again depend upon the patient's state of health and general level of immunity.

Single or multiple administrations of the compositions can be carried out with dose levels and pattern being selected by the treating physician. In any event, the pharmaceutical formulations should provide a quantity of the antineoplastic replication deficient adenoviruses of this invention sufficient to effectively treat the patient.

Antineoplastic replication deficient adenoviral therapy of the present invention may be combined with other antineoplastic protocols, such as conventional chemotherapy.

Propagation of Mutant Adenovirus

Adenoviral mutants of the invention (e.g., E1a-RB$^{(-)}$ replication deficient adenoviruses, E1b-p53$^{(-)}$ replication deficient adenoviruses, and E1a/E1b double mutants) typically are propagated as viral stocks in a cell line (e.g., the 293 cell line ATCC # CRL 1573, American Type Culture Collection, Rockville, Md.; Graham et al. (1977) *J. Gen. Virol.* 36: 59) which can provide E1a function, E1b function, or both E1a and E1b functions, respectively, in trans to support replication and formation of infectious mutant virions.

The following examples are offered by way of example and not by way of limitation. Variations and alternate embodiments will be apparent to those of skill in the art.

EXPERIMENTAL EXAMPLE

The following experimental example demonstrates that administering a replication-deficient recombinant adenovirus preparation to neoplastic cells lacking p53 and/or Rb function can effectively kill neoplastic cells. The example also shows that non-neoplastic cells containing p53 and Rb function are relatively resistant to killing by the replication-deficient recombinant adenovirus preparation. Therefore, the data presented hereinbelow provide experimental verification that administration of replication-deficient recombinant adenovirus can be used to selectively kill neoplastic cells. The selective killing is provided by exploiting the differential ability of the mutant adenoviruses to induce a replication phenotype in neoplastic cells, but substantially not induce a replication phenotype (or associated cytopathic effect) in non-neoplastic cells.

Control non-neoplastic cells and cell lines representing a variety of neoplastic cell types were plated in 6-well culture dishes at or near confluence in DMEM (high glucose) with 10% fetal bovine serum and incubated at 37° C., 5% $CO_2$ under standard culturing conditions. Cells were plated to be screened at a density of $5\times10^5$ cells/well. The neoplastic cell lines tested were: SAOS-2 (ATCC HTB85), derived from a human primary osteogenic sarcoma; U-20S (ATCC HTB96), derived from a human osteogenic sarcoma; HS700T, (ATCC HTB147), derived from a human metastatic adenocarcinoma originating in the pancreas or intestines; 293 (ATCC CRL1573), transformed human embryonal kidney; and DLD-1 (ATCC CCL221), derived from a human colon adenocarcinoma. Each of the cell lines is available from American Type Culture Collection, Rockville, Md. The control non-neoplastic cells were IMR90 (ATCC CCL 186) and WI-38 (ATCC CCL 75), both diploid human lung fibroblast lines.

These cell cultures were subsequently infected, in parallel, with wild-type adenovirus Type 2, and replication-deficient recombinant adenovirus mutants dl 11010, dl 434, and dl 1520. An extra culture dish was plated for the purpose of counting cells. These cells came from the same suspension of cells used for the viral infections. Cells were counted in order to determine the number of viral plaque-forming units (PFU) to add to the cell cultures for a desired multiplicity of infection (MOI). The wild-type adenovirus Type 2 and the mutant adenoviruses were added to the parallel cell cultures at MOIs of 0.1, 1.0, 10, and 100. Virus suspended in PBS was added to the cell wells in a volume of 1 ml. The inoculated culture dishes were rocked in both the X- and Y-axes immediately after inoculation and halfway through the adsorption time of approximately one hour at 37° C., 5% $CO_2$. After the one hour adsorption period, 2 ml of DMEM with high glucose and 2% fetal bovine serum was added, and the cultures incubated at 37° C., 5% $CO_2$ under standard culturing conditions.

At various times after infection, see, FIG. 2(a–i), cell cultures were stained with 0.5% crystal violet in 20% methanol in order to determine the efficacy of cell killing by the virus preparations. Dead cells were detached and rinsed out of the wells, whereas living cells remained in the well and were stained with the dye. The results demonstrate that the replication-deficient recombinant adenovirus preparations were able to preferentially kill neoplastic cells as compared to non-neoplastic cells, and that wild-type adenovirus Type 2 killed both neoplastic and non-neoplastic cells approximately equally well. The results demonstrate that the dl 11010 mutant was particularly effective at killing neoplastic cells, with the dl 1520 mutant and the dl 434 mutant also being effective. An example of the results is shown in FIG. 2a–i, which are photographs of the stained cell wells obtained at various times after infection with wild-type adenovirus 2, the mutants: dl 1010 (E1A$^{(-)}$), dl1520 (E1B$^{(-)}$), or dl 434. FIG. 2a shows that in the absence of virus, each of the cell cultures had grown to confluence and were attached to the culture wells. FIG. 2b–c shows that wild-type adenovirus 2 was able to kill cells in each of the culture wells, although with variable efficacy and incompletely, with at least some cells staining in each well. Note that WI-38 and SAOS-2 lines are not good hosts for adenovirus infection and that IMR90 (FIG. 3a–c) serves as an alternate control cell line for human diploid fibroblasts. FIG. 2d–e shows that the dl 1010 mutant was able to kill effectively all of the neoplastic cell lines except the infection-resistant SAOS-2. dl 1010 killed the 293, U20S, HS700T, and DLD-1 lines by 12 days after infection and did not substantially kill diploid human lung fibroblasts (WI-38). FIG. 2f–g shows that the dl 1520 mutant was able to kill effectively 3 of the 5 neoplastic cell lines (293, HS700T, and DLD-1) by 14–20 days after infection and did not substantially kill diploid human lung fibroblasts (WI-38). dl 1520 is an E1B$^{(-)}$ mutant, and cell line U20S does not allow such an E1B$^{(-)}$ mutant virus to replicate, indicating specificity of the different transformed cell lines for infection by the mutant recombination-defective adenoviruses, as predicted. FIG. 2h–i shows that the dl 434 mutant (a double-mutant: E1A$^{(-)}$ E1B$^{(-)}$) was able to kill effectively 3 of the 5 neoplastic cell lines (293, HS700T, and DLD-1) by 14–20 days after infection and did not substantially kill diploid human lung fibroblasts (WI-38). The DLD-1 and U20S lines displayed a partially resistant phenotype for replication of dl 434.

Figure 3A:
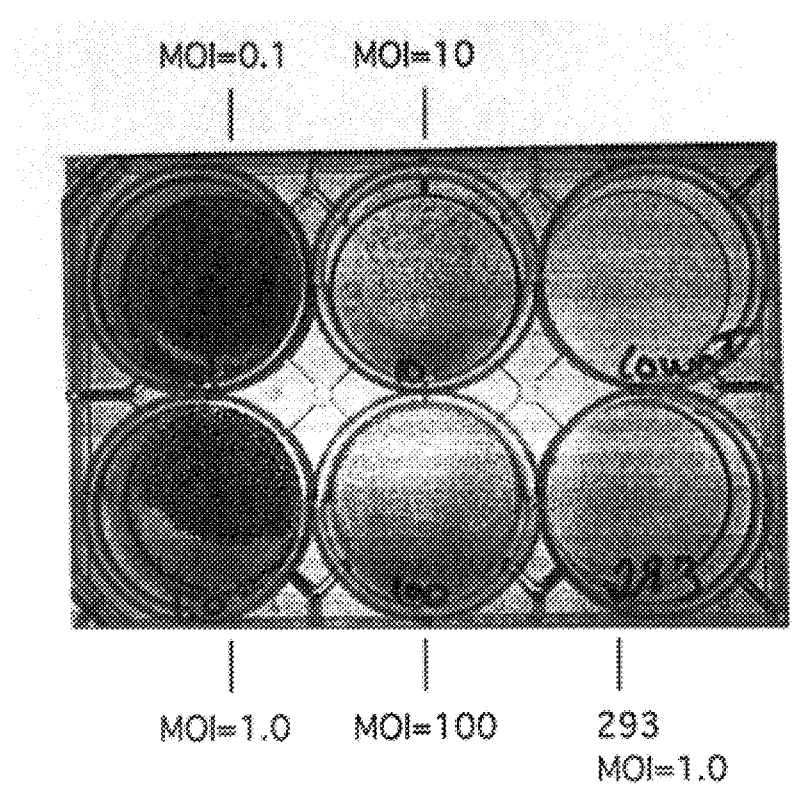
FIG. 3(a) shows cells infected with wild-type Ad2 at 9 days post-infection.
Figure 3B:
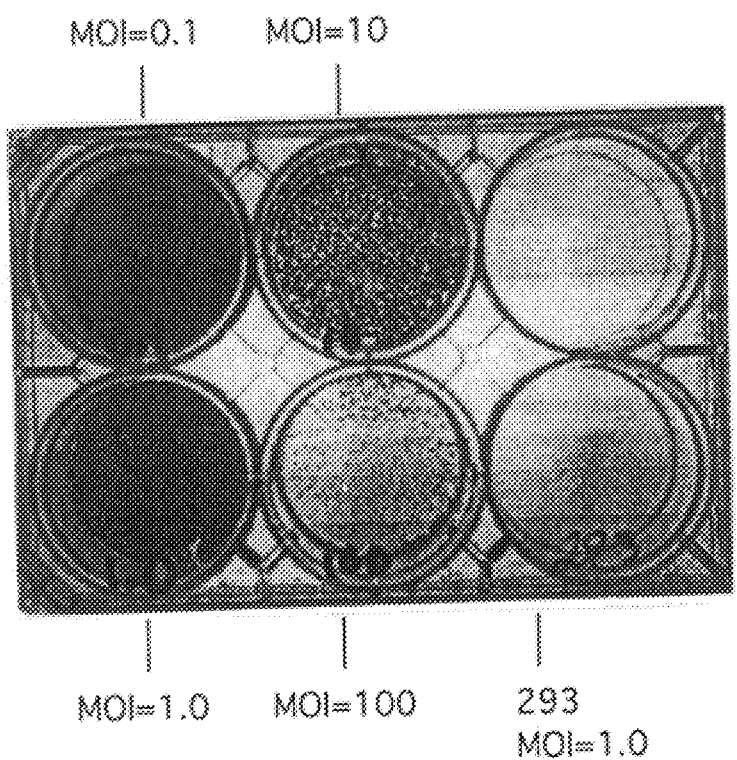
FIG. 3(b) shows cells infected with dl 1010 at 9 days post-infection.
Figure 3C:
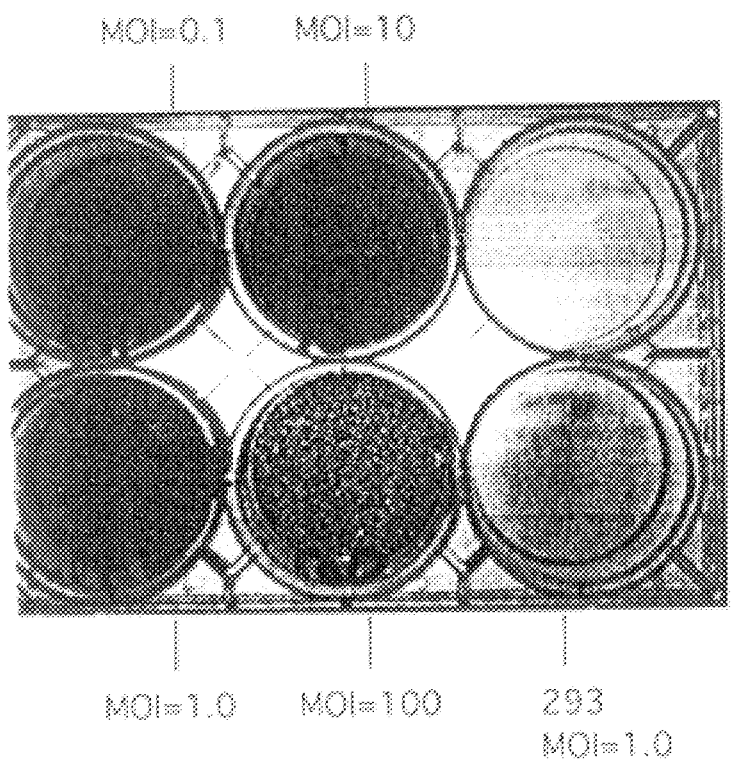
FIG. 3(c) shows cells infected with dl 1520 at 9 days post-infection.

FIG. 3(a–c) show that IMR90 human diploid lung fibroblasts were killed differentially by wild-type Ad2, dl 1010, and dl 1520. The 293 cell line serves as a positive control. FIG. 3(a) shows that wild-type Ad2 killed the IMR90 cells effectively at an MOI of 10 or 100. FIG. 3(b) shows that dl 1010 was unable to replicate in IMR90 cells at the highest MOI tested, even though dl 1010 killed neoplastic cell lines 293, U20S, HS700T, and DLD-1 as shown in FIG. 2(d-e). FIG. 3(c) shows that dl 1520 virus was able to kill IMR90 cells effectively only at an MOI of 100; at this high dosage of virus the possibility that the cells die as a result of virus overload rather than replication cannot be ruled out.

Thus, the data shown in FIGS. 2(a–i) and 3(a–c) indicate that replication-deficient recombinant adenovirus mutants can be used to selectively kill neoplastic cells lacking p53 and/or Rb function, as predicted.

Although the present invention has been described in some detail by way of illustration for purposes of clarity of understanding, it will be apparent that certain changes and modifications may be practiced within the scope of the claims.

I claim:

1. A method for ablating neoplastic cells in a cell population, comprising the steps of:
   contacting under infective conditions (1) a recombinant replication deficient adenovirus lacking an expressed viral oncoprotein which binds a functional p53 tumor suppressor gene product, with (2) a cell population comprising non-neoplastic cells containing said functional p53 tumor suppressor gene product which forms a bound complex with a viral oncoprotein and neoplastic cells lacking said functional p53 tumor suppressor gene product, thereby generating an infected cell population, and a chemotherapeutic.

2. A method according to claim 1, wherein the viral oncoprotein is an adenovirus E1a polypeptide or an adenovirus E1b polypeptide.

3. An anti-neoplastic composition for therapy of neoplastic disease, comprising a therapeutically effective dosage of a recombinant replication deficient adenovirus, said virus lacking an expressed viral oncoprotein which binds a functional p53 tumor suppressor gene product, and which replicates in neoplastic cells that substantially lack functional p53, and a chemotherapeutic.

4. An anti-neoplastic composition for therapy of neoplastic disease as described in claim 3 wherein said recombinant replication deficient adenovirus is E1b p53$^{(-)}$.

5. An anti-neoplastic composition for therapy of neoplastic disease as described in claim 4 wherein said recombinant replication deficient adenovirus is Ad2 dl1520.

* * * * *